United States Patent [19]
Larsen et al.

[11] Patent Number: 5,874,547
[45] Date of Patent: Feb. 23, 1999

[54] DIAZOTIZATION OF AMINES

[75] Inventors: John W. Larsen; Tracey McCracken, both of Bethlehem; Jay E. Rowe, Mohnton; Lee A. Schaeffer, Mertztown, all of Pa.

[73] Assignee: Crompton & Knowles Corporation, Stamford, Conn.

[21] Appl. No.: 869,756

[22] Filed: Jun. 5, 1997

Related U.S. Application Data

[60] Provisional application No. 60/019,342, Jun. 6, 1996.
[51] Int. Cl.$^6$ .................................................. C07C 245/20
[52] U.S. Cl. ........................ 534/565; 534/642; 534/834; 534/839; 534/842; 534/861; 534/887
[58] Field of Search ............................................. 534/565

[56] References Cited

U.S. PATENT DOCUMENTS

| | | | |
|---|---|---|---|
| 2,769,832 | 11/1956 | Reilly | 534/565 X |
| 2,829,029 | 4/1958 | Bachman et al. | 534/565 X |
| 2,894,941 | 7/1959 | Bachman et al. | 534/565 |
| 3,160,623 | 12/1964 | Anello et al. | 534/565 |
| 3,380,988 | 4/1968 | Rigaudy | 534/565 X |
| 4,020,052 | 4/1977 | Detrick | 534/565 X |
| 4,269,767 | 5/1981 | Ratton | 534/565 |
| 4,918,168 | 4/1990 | Stepaniuk et al. | 534/565 |
| 5,393,874 | 2/1995 | Massonne et al. | 534/556 |

OTHER PUBLICATIONS

Wink, D.A. et al., "DNA Deaminating Ability and Genotoxicity of Nitric Oxide and its Progenitors," Science, vol. 254, 1001–03 (15 Nov. 1991).

Zollinger, H., "History of Aromatic and Heteroaromatic Diazo Compounds," Diazo Chemistry, vol. I, 1–10 (1994).

Zollinger, H., "Methods for the Preparation of Aromatic and Heteroaromatic Diazo Compounds" Diazo Chemistry, vol. II, 11–25 (1994).

*Primary Examiner*—Fiona T. Powers
*Attorney, Agent, or Firm*—Daniel Reitenbach; Paul Grandinetti

[57] ABSTRACT

A process for diazotizing an amine comprises the steps of oxidizing nitric oxide in solution with an oxidizing agent to maintain an equilibrium concentration of a diazotizing agent and reacting a primary aromatic amine in situ with said diazotizing agent in said solution.

10 Claims, No Drawings

DIAZOTIZATION OF AMINES

The applicants claim the benefit of U.S. Provisional Application Serial No. 60/019,342 filed on Jun. 6,1996.

BACKGROUND OF THE INVENTION

1. Field of the Invention

The invention relates to a diazotization process for amines. More particularly, the invention relates to a diazotization process for producing azo dye compounds.

2. Description of Related Art

Numerous diazotization processes for primary aromatic amines are known. Many of these processes are commercially important because of their use in the production of dyestuffs. The most commercially significant diazotization processes are batch processes carried out at temperatures from −5° to +5° C. and use nitrous acid (HONO) as the diazotizing agent. It is formed in situ from $NaNO_2$ and HCl producing significant amounts of salt that must be separated from the dye and discarded as hazardous waste. In most processes, a large excess of HCl is used. This is neutralized during the ensuing coupling reaction producing more salt that also must be removed and discarded. Both the separation and disposal of the salt are costly procedures. To form an azo dye, the aromatic diazonium ion is coupled with a second electron rich molecule (i.e. coupler) or coupling agent to form the dye.

Some unreactive or insoluble amines cannot be diazotized in aqueous solution. Many of these are diazotized using nitrosylsulfuric acid prepared by dissolving sodium nitrite in 90 to 96 percent sulfuric acid at 0° C. to 10° C. The nitrosylsulfuric acid is added to a solution of the arylamine in 96 percent sulfuric acid at 0° C. to 10° C. The diazonium compound is then coupled with an amine, a phenol, or any molecule which offers electron pair availability to form an azo linkage.

A process for producing diazonium ions without by-product salt would offer advantages and be environmentally desirable. No such commercial process is known to be in operation.

SUMMARY OF THE INVENTION

The invention is a process for the diazotization of a wide variety of aromatic primary amines without generation of inorganic salts. The invention includes the step of oxidizing nitric oxide with an oxidizing agent to maintain an equilibrium concentration of a diazotizing agent. The invention further includes the step of reacting a primary amine in situ with said diazotizing agent in said aqueous solution.

DESCRIPTION OF THE PREFERRED EMBODIMENTS

The invention is a process for the diazotization of a primary aromatic amine to produce a diazonium salt. In addition, the invention is a process for producing azo compounds and, in particular, azo dyes. The process provides an oxidizing agent for reaction with nitric oxide to produce a diazotizing agent. The reaction is desirably performed in an acidic aqueous solution, but can be performed in a non-aqueous liquid such as acetic acid. A desirable oxidizing agent is a member selected from the group consisting of oxygen, hydrogen peroxide, sodium hypochlorite, potassium chlorate, sodium perchlorate, sodium bromate, sodium iodate, mixtures of these and oxidizing agents having a half-reaction electrode potential favorable to the oxidation of nitric oxide.

There are two different desirable ways of carrying out the oxidation. One mixes air and NO in situ in the presence of a primary aromatic amine to form the diazonium ion as shown in Equation 1.

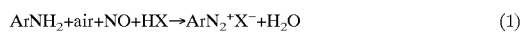

$$ArNH_2 + air + NO + HX \rightarrow ArN_2^+ X^- + H_2O \quad (1)$$

The second method uses an aqueous solution of any of a number of oxidizing agents designated by "O" in Equation 2.

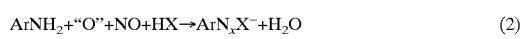

$$ArNH_2 + \text{"O"} + NO + HX \rightarrow ArN_xX^- + H_2O \quad (2)$$

Examples of "O" include but are not limited to NaOCl (household bleach) and hydrogen peroxide. The aromatic amines can be any of the wide variety of primary amines used to form azo dyes as well as others.

This invention provides the desirable effect of diazotizing aromatic amines that are currently diazotized using sodium nitrite (NaNO2) and hydrochloric acid (HCl) as well as many aromatic amines that require nitrosylsulfuric acid for diazotization. Such amines can be characterized by the formulas

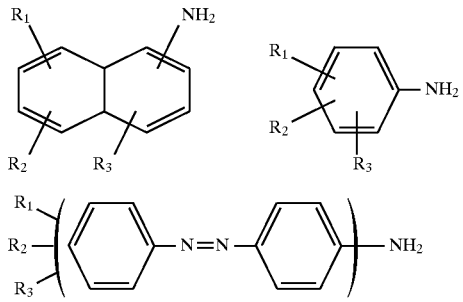

wherein $R_1$, $R_2$ and $R_3$ can be, independently, hydrogen, —$SO_3H$, —$CO^2H$, $C_1$–$C_6$ alkyl, $C_1$–$C_6$— alkoxy, halogen $C_2$–$C_6$ alkanoylamino, unsubstituted or substituted arylsulfonyl, sulfatoethyl sulfonyl, aryloxy, arylcarbonyl, phenylazo, naphthylazo, nitro radicals, or radicals of the formula

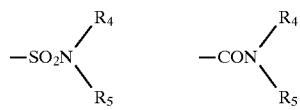

wherein $R_4$ and $R_5$ are $C_1$–$C_6$ alkyl or cycloalkyl or $R_4$ and $R_5$ constitute together a cyclic alkyl, cyclic alkylether or cyclic alkylamine.

The amines of the above formulas are known or can be prepared by those skilled in the art. Representative examples include, but are not limited to, a wide range of diazotizable amines, such as, aniline, o-toluidine, m-toluidine, p-toluidine, p-butylaniline, 2,4-xylidine, p-dodecylaniline, 4-amino-3-nitroacetanilide, 5-acetamino-2-aminophenol-3-sulfonic acid, m-aminoacetanilide, p-aminoacetanilide, 3-amino-4-methylacetanilide, 4-aminoacetanilide-3-sulfonic acid, 2-amino-4-acetamidophenylmethyl sulfone, p-nitroaniline, 2-methyl-4-nitroaniline, 2,4-dinitroaniline, 6-bromo-2,4-dinitroaniline, 2-amino-4-nitrophenol, 2-amino-5-nitrophenol, 2-amino-4-methyl-6-nitrophenol, 2-amino-4-chloro-6-nitrophenol, 2-amino-4-nitrophenol-6-sulfonic acid, 4-amino-N-methylacetanilide, 2-amino-5-nitrobenzoic acid, 2-amino-6-nitro-4-sulfobenzoic acid, 2-methoxy-4-nitroaniline, 4-methoxy-2-nitroaniline, 4-chloro-2-nitroaniline, 2-bromo-6-methyl-4-nitroaniline, 2,6-dichloro-4-nitroaniline, 2,6-dibromo-4-nitroaniline, 4-nitroaniline-2-sulfonic acid, 2-aminophenol, 2-amino-4-methylphenol, 2-amino-4-chlorophenol, 2-amino-5-methylsulfonylphenol, 2-aminophenol-4-sulfonamide, 2-aminophenol-4-N-methylsulfonamide, 2-aminophenol-4-sulfonic acid, 3-aminoacetophenone, anthranilic acid, o-anisidine, p-cresidine, dimethoxy para base, para base sulfate, dimethoxy para base sulfate, 2-chloroaniline, 4-chloroaniline, 2,6-dichloroaniline, 2-aminobenzotrifluoride, 2-amino-5-chlorobenzotrifluoride, 2,5-dichloroaniline-4-sulfonic acid, 2-chloroaniline-5-sulfonic acid, orthanilic acid, metanilic acid, sulfanilic acid, 4-amino-4'-nitrodiphenylamine-2'-sulfonic acid, 4-aminoazobenzene-4'-sulfonic acid, 2-amino-N-ethyl-N-phenylbenzenesulfonamide, 2-naphthylamine-6-sulfonic acid, 2-naphthylamine-4,8-disulfonic acid, 2-amino-8-naphthol-6-sulfonic acid, 1-amino-8-naphthol-3,6-disulfonic acid, 4-aminoazobenzene-3'-sulfonic acid, 2-naphthylamine-1-sulfonic acid, 2-naphthylamine-6-sulfonic acid, 2-amino-1,1'-diphenylsulfone, 2-amino-N-cyclohexyl-N-methylbenzenesulfonamide and 1-[(2-aminophenyl)sulfonyl]azacycloheptane.

The preferred process combines nitric oxide and air in contact with the reaction medium to produce a diazofizing solution. The nitric oxide gas is delivered to the reaction at any effective pressure. Desirable delivery pressures can be atmospheric or higher pressures, and only the amount of nitric oxide required for the reaction is consumed by the process. This process permits the nitric oxide consumption or "uptake" to be monitored as the reaction progresses. The diazotization reaction is rapid. In this series of reactions, NO is introduced into a closed flask containing air and the NO uptake monitored as with time using a gas burette.

In the series of reactions in Table 1, NO is introduced into a closed flask containing air and the NO uptake is monitored as with time using a gas burette. The times listed are those at which NO uptake is complete. These data demonstrate the rapidity of the reaction forming diazonium ions. These diazonium ions are then reacted with alkaline 2-naphthol to give the azo dye whose crude and recrystallized yields are given. Diazonium ion formation is both rapid and nearly quantitative.

TABLE 1

Yields and Reaction Times - NO/Air/HNO$_3$ Method

|  | Crude Yield | Recrystallized Yield | Reaction Time (min.) |
|---|---|---|---|
| Aniline | 97% | 88% | 3 |
| p-Toluidine | 92% | 64% | 4 |
| Metanilic Acid | 95% | 72% | 3 |

Nitric oxide, an oxidant, such as air, and an acid are necessary for diazotization. The requirement for these three components is demonstrated by three experiments.

The requirement for nitric oxide is shown by adding aniline to a cold acidic solution of oxidant, such as air, and vigorously stirring the mixture. Thin-layer chromatography (TLC) can be used to follow the composition of the reaction mixture over time. When nitric oxide is not added, the aniline TLC spot, after two hours, is the only spot observed. Therefore, the observed reaction of the aniline requires nitric oxide.

The requirement for an acid is shown by permitting nitric oxide to enter a reaction vessel containing air, wherein no acid is present. A reverse addition of this reaction mixture to an alkaline 2-naphthol solution does not produce a color change and does not precipitate crystals. Thin-layer chromatography shows no new spots after two hours, and only aniline is present. Therefore, the acid is necessary for diazotization.

Introduction of NO into a closed air-free reactor containing an aqueous solution of aniline in nitric acid resulted in no detectable diazotization. This demonstrates the necessity of the oxidizing agent.

Many known commercial processes employ about 2.5 equivalents of hydrochloric acid for the diazotization procedure. When this acid is subsequently neutralized with sodium hydroxide, bicarbonate or carbonate, 2.5 equivalents of sodium chloride are produced. In contrast, the pH of the reaction solution of the invention can be changed from about pH 2 to neutral with the addition of a trivial amount of alkali.

The diazotization reaction and the coupling reaction are performed in an aqueous medium at a temperature in the range of from −5° to 25° C., more preferably, 0° C. to 5° C. Once the diazonium salt is produced, it is combined with the coupling agent. The coupling agent can be any electron rich organic chemical structure capable of participating in electrophilic substitution. Suitable coupling components include, but are not necessarily limited to, compounds with activated methyl or methylene groups, aromatic hydroxyl compounds possessing ortho or para ring positions, and aromatic amines having available electron-rich ortho or para ring positions.

Suitable examples of activated methyl or methylene groups include, but are not limited to, acetoacetic acid esters, acetoacetanilides, and orthomethyl quaternary heterocycles.

Suitable examples of activated phenolic type molecules include, but are not limited to, phenol, substituted phenols, 2-naphthol and substituted 2-naphthols, α-naphthol and substituted α-naphthols.

Suitable examples of aromatic amines include aniline, substituted anilines, alkylanilines, substituted alkylanilines, β-naphthylamines, and substituted β-naphthylamines.

The invention is directed to a method of diazotization to produce diazonium salts. The subsequent reaction to which the diazonium compound is directed is determined by control of the reaction conditions, components, and environment. Once the diazonium compound is produced, it can be utilized in any chemical process known for such materials by one skilled in the art.

The counter ion X is the anion of a strong mineral acid. The acid used will be selected on the basis of ancillary considerations such as environmental impact, product physical character, filtration rate and corrosion, costs etc. Mixtures of acids may be used as shown in Reaction Scheme 1, carried out using both sulfuric and nitric acid to produce a mixture of anions.

Reaction Scheme 1

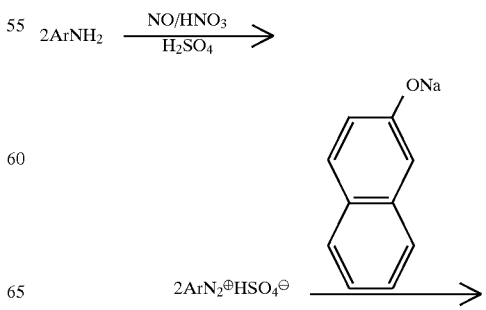

$2ArNH_2 \xrightarrow[H_2SO_4]{NO/HNO_3}$ $2ArN_2^{\oplus}HSO_4^{\ominus} \longrightarrow$ Reaction Scheme 1

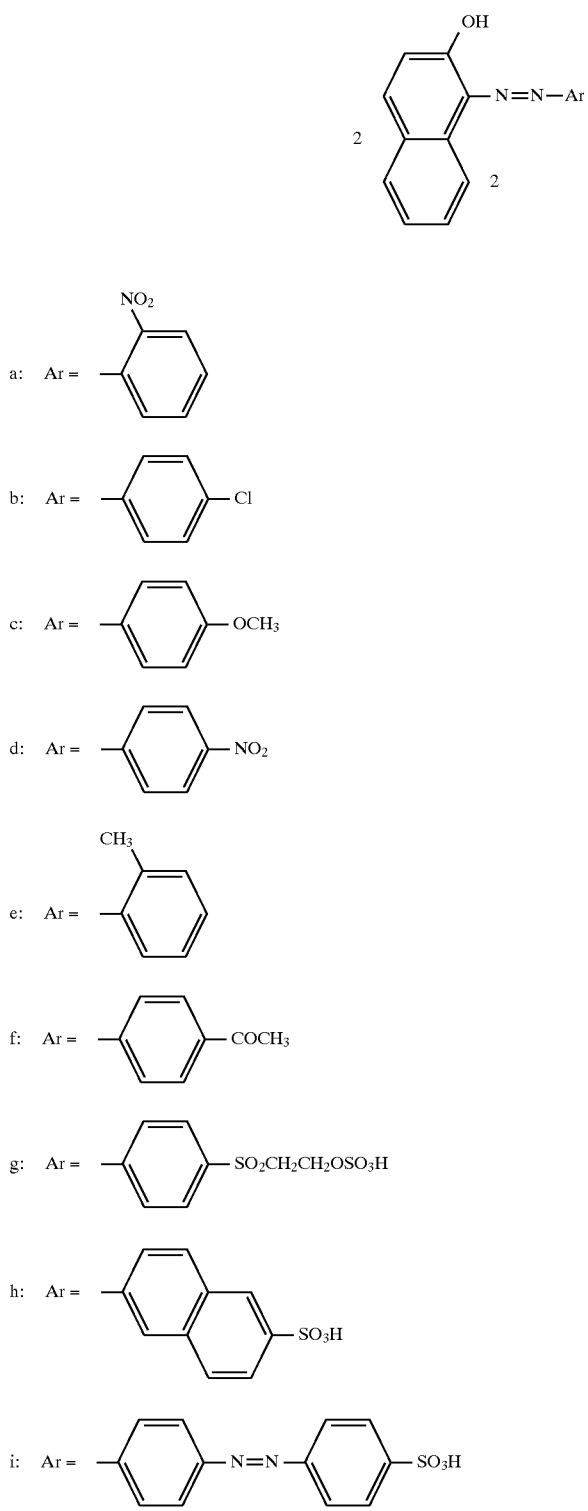

Yields for these reactions are about 88 to 96 percent. The diazonium ions were trapped using 2-naphthol.

Table 2 presents the results for this series of compounds diazotized using the nitric oxide and nitric acid method with sulfuric acid as a counterion.

TABLE 2

Yields and Reaction Times - NO/air/HNO$_3$ & H$_2$SO$_4$

| | Crude Yield | Recrystallized Yield | Reaction Time (min.) |
|---|---|---|---|
| a: o-nitroaniline | 90% | 84% | 3 |
| b: p-chloroaniline | 93% | 84% | 2.5 |
| c: p-anisidine | 88% | 76% | 2.5 |
| d: p-nitroaniline | 93% | 83% | 3 |
| e: o-toluidine | 90% | 87% | 3 |
| f: 4'-aminoacetophenone | 88% | 85% | 3 |
| g: Para Base Sulfate | 90% | 86% | 15 |
| h: Broenner's Acid | 96% | 90% | 22 |
| i: 4-Aminoazobenzene-4'-sulfonic acid | 91% | 86% | 28 |

This reaction can also be carried out by simultaneously introducing NO and air into the flask by using two gaseous feed systems. In practice, air is bubbled through a cooled (-5° C.) aqueous acid containing aniline. This solution absorbs nitric oxide from a reservoir at one atmosphere of pressure and the aniline diazonium ion is produced. Table 3 presents the results of the diazotization procedure for a series of amines illustrated in Reaction Scheme 2. Again, yields are high and reactions are rapid. Also, a condition that is important in industry exists wherein the reaction of the invention often permits higher concentrations and, therefore, increased amounts of dyes to be produced using the same size apparatus.

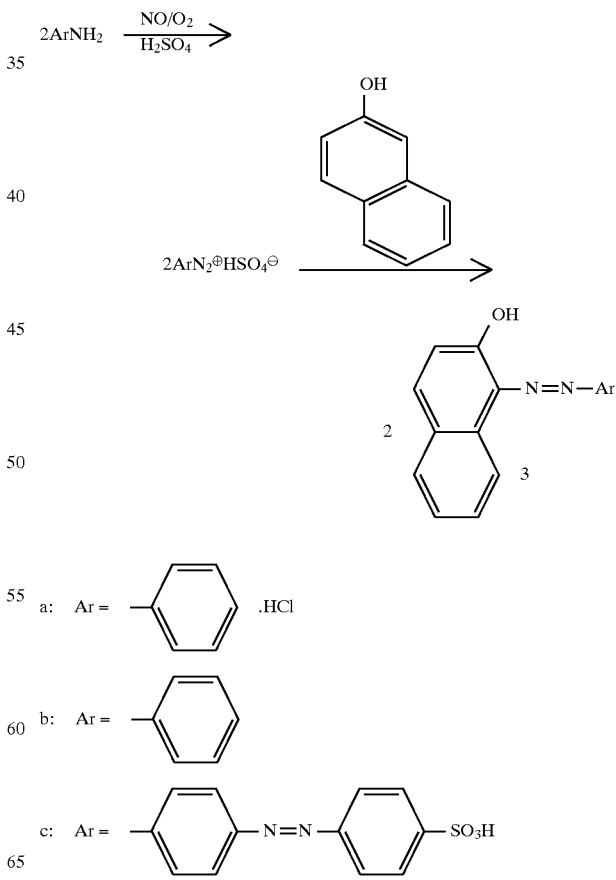

-continued
Reaction Scheme 2

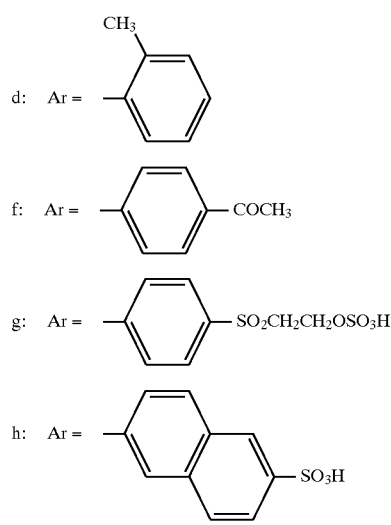

d: Ar = [2-methylphenyl]

f: Ar = [4-acetylphenyl-COCH₃]

g: Ar = [phenyl-SO₂CH₂CH₂OSO₃H]

h: Ar = [naphthyl-SO₃H]

TABLE 3

Yields and Reaction Times - flowing air/NO/HX

| | Crude Yield | Recrystallized Yield | Reaction Time (min.) |
|---|---|---|---|
| a: aniline hydrochloride | 90% | 85% | 3 |
| b: aniline | 94% | 86% | 3 |
| c: Aminoazobenzene-4'-sulfonic acid | 90% | 85% | 5 |
| d: o-toluidine | 91% | 85% | 5 |
| e: p-nitroaniline | 95% | 87% | 3 |
| f: 4'-Aminoacetophenone | 91% | 85% | 4 |
| g: Para Base Sulfate | 91% | 83% | 5 |
| h: Broenner's acid | 91% | 86% | 5 |

Suitable oxidants for this invention are those oxidants that can sustain an equilibrium of the oxidation reaction of nitric oxide to nitrous acid in aqueous solution. Desirable oxidants have an electrode potential suitable for the oxidation reaction of nitric oxide. Examples of electrode potentials for suitable oxidants are presented in Table 4.

TABLE 4

Electrode Potential (E°) for Oxidants[1]

| Oxidant | Electrode Potential[2] |
|---|---|
| Hydrogen Peroxide ($H_2O_2$) | +0.793 V |
| Sodium Hypochlorite (NaOCl) | +0.6547 V |
| Potassium Chlorate ($KClO_3$) | +0.468 V |
| Sodium Perchlorate ($NaClO_4$) | +0.406 V |
| Sodium Iodate ($NaIO_3$) | +0.102 V |
| Sodium Sulfate ($Na_2SO_4$)[3] | −1.0853 V |

[1]The electrode potential (E°) is the difference between the electrode potential for the oxidation of nitric oxide (E° = −0.983 V) and the electrode potential for the oxidant.
[2]A positive value in the electrode potential difference indicates that the reaction is thermodynamically feasible.
[3]Diazotization did not occur.

The oxidants of Table 4 have a half cell potential sufficient to generate nitrous acid from nitric oxide. Suitable oxidants include an inorganic oxidant being a member selected from the group consisting of chromates, perchromates, perhalogenates, peracids, perbenzoic acids, peracetic acids, and mixtures of these. The most desirable oxidant for the invention is a member selected from the group consisting of nitric acid, oxygen, hydrogen peroxide, sodium hypochlorite, potassium chlorate, sodium perchlorate, sodium bromate, sodium iodate, and mixtures of these.

EXAMPLES

The following examples illustrate various embodiments of the invention. The general procedure of the examples is as follows.

The reagents of aniline, substituted anilines, nitric acid, sulfuric acid, sodium nitrite, sodium bicarbonate, and 2-naphthol are purchased from Aldrich Chemical Company, Milwaukee, Wis., and are used without further purification. The reagents Broenner's acid, Para Base Sulfate, 4-Aminoazobenzene-4'-sulfonic acid, N-acetyl J acid, and H acid are industrial grade and are obtained from Crompton & Knowles Colors Incorporated in Gibraltar, Pa. They are used without further purification.

All syntheses are performed "cold" or from about 0° C. to about 5° C. using an ice bath and are stirred vigorously with a magnetic stirrer. Sulfuric acid is added using a three-cubic centimeters syringe.

Air, when used, is delivered to the systems, as required, by an aquarium pump attached to a bubbling tube submerged in the reaction mixture. The nitric oxide gas is also delivered by a submerged bubbling tube.

Comparative Example

This comparative example produces a commercially available golden orange dye. This comparative example represents the background art and does not represent the invention. C.I. Reactive Orange 72

46.5 grams (0.165 mol) Para Base Sulfate was added to 112.5 milliliters of water with stirring and dissolved by addition of 16.1 grams of sodium bicarbonate. The solution was cooled to 0° C. by addition of ice and treated with 39.8 grams of muriatic acid. The Para Base Sulfate was then diazotized by addition of 16.5 grams (0.152 mol) of sodium nitrite. The diazo was stirred for 1.5 hours at 0°–5° C. before removal of excess nitrous acid with sulfamic acid. The diazo was coupled to form Reactive Orange 72 by addition of 53.7 grams (0.160 mol) of N-Acetyl J Acid. The coupling was driven to completion by addition of 17.4 grams of sodium bicarbonate. The production was isolated by filtration to yield 83.0 grams (89.6% yield) of orange dye.

This comparative example produces the golden orange dye along with salt. The salt is a waste by-product. The diazotization procedure of this comparative example progresses slowly.

EXAMPLES 1 THROUGH 10

Diazotization with Nitric Acid and Sulfuric Acid-Closed Air-Filled Flask (Reaction Scheme 1)

Examples 1 through 10 represent the invention. A diazotization procedure is performed in these examples with nitric acid and sulfuric acid.

Example 1

This example produces 1-phenylazo-2-naphthol. The general procedure explained above is used for this example.

A quantity of 1.5 milliliters (0.016 mol) of aniline is added to 20 milliliters of water containing 0.50 milliliter (0.079 mol) of nitric acid and 0.45 milliliter (0.016 mol) of sulfuric acid. Nitric oxide gas ($NO_{(g)}$) is allowed to flow into the closed air filled reaction flask. Diazotization time is three minutes. Reverse addition to a cold 10 percent aqueous sodium hydroxide (NaOH) solution containing 2.392 grams (0.017 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 91 percent. The yield of the dye recrystallized from glacial acetic acid is 77 percent.

Example 2

This example produces 4'-[2-hydroxy-naphthyl-1-azo]-azobenzol-4-sulfonic acid. The general procedure explained above is used for this example.

A quantity of 4.46 grams (0.016 mol) of 4-aminoazobenzene-4'-sulfonic acid is added to 20 milliliters of water containing 0.34 milliliter (0.054 mol) of nitric acid and 0.45 milliliter (0.016 mol) of sulfuric acid. Nitric oxide gas is allowed to flow into the closed air filled reaction flask. Diazotization time is 28 minutes. Reverse addition to a cold 10 percent aqueous sodium hydroxide solution containing 2.392 grams (0.017 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 91 percent. The yield of the dye recrystallized from glacial acetic acid is 86 percent.

Example 3

This example produces 1-[4-chloro-phenylazo]-2-naphthol. The general procedure explained above is used for this example.

A quantity of 1.814 grams (0.014 mol) of p-chloroaniline is added to 20 milliliters of water containing 0.30 milliliter (0.047 mol) of nitric acid and 0.45 milliliter (0.016 mol) of sulfuric acid. Nitric oxide gas is allowed to flow into the closed air-filled reaction flask. Diazotization time is 2.5 minutes. Reverse addition to a cold 10 percent aqueous sodium hydroxide solution containing 2.116 grams (0.015 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 93 percent. The yield of the dye recrystallized from glacial acetic acid is 84 percent.

Example 4

This example produces 1-[4-methoxy-phenylazo]-2-naphthol. The general procedure explained above is used for this example.

A quantity of 1.984 grams of p-anisidine (0.016 mol) is added to 20 milliliters of water containing 0.34 milliliter (0.053 mol) of nitric acid and 0.45 milliliter (0.016 mol) of sulfuric acid. Nitric oxide gas is allowed to flow into the closed air-filled reaction flask. Diazotization time is 2.5 minutes. Reverse addition to a cold 10 percent aqueous sodium hydroxide solution containing 2.414 grams (0.017 mol) 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 88 percent. The yield of the dye recrystallized from glacial acetic acid is 76 percent.

Example 5

This example produces 1-o-tolylazo-2-naphthol. The general procedure explained above is used for this example.

A quantity of 1.75 milliliters (0.016 mol) of o-toluidine is added to 20 milliliters of water containing 0.34 milliliter (0.053 mol) of nitric acid and 0.45 milliliter (0.016 mol) of sulfuric acid. Nitric oxide gas is allowed to flow into the closed air-filled reaction flask. Diazotization time is three minutes. Reverse addition to a cold 10 percent aqueous sodium hydroxide solution containing 2.418 grams (0.17 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 91 percent. The yield of the dye recrystallized from glacial acetic acid is 87 percent.

Example 6

This example performs diazotization of p-nitroaniline. The general procedure explained above is used for this example.

A quantity of 2.225 grams (0.016 mol) of p-nitroaniline is added to 20 milliliters of water containing 0.34 milliliter (0.053 mol) of nitric acid and 0.45 milliliter (0.016 mol) of sulfuric acid. Nitric oxide gas is allowed to flow into the closed air-filled reaction flask. Diazotization time is three minutes. Reverse addition to a cold 10 percent aqueous sodium hydroxide solution containing 2.397 grams (0.17 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 93 percent. The yield of the dye recrystallized from glacial acetic acid is 83 percent.

Example 7

This example performs diazotization of o-nitroaniline. The general procedure explained above is used for this example.

A quantity of 2.225 grams (0.016 mol) of o-nitroaniline is added to 20 milliliters of water containing 0.34 milliliter (0.053 mol) of nitric acid and 0.45 milliliter (0.016 mol) of sulfuric acid. Nitric oxide gas is allowed to flow into the closed air-filled reaction flask. Diazotization time is four minutes. Reverse addition to a cold 10 percent aqueous sodium hydroxide solution containing 2.390 grams (0.16 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 90 percent. The yield of the dye recrystallized from glacial acetic acid is 84 percent.

Example 8

This example performs diazotization of 4'-aminoacetophenone. The general procedure explained above is used for this example.

A quantity of 2.177 grams (0.016 mol) of 4'-aminoacetophenone is added to 20 milliliters of water containing 0.34 milliliter (0.053 mol) of nitric acid and 0.45 milliliter (0.016 mol) of sulfuric acid. Nitric oxide gas is allowed to flow into the closed air-filled reaction flask. Diazotization time is three minutes. Reverse addition to a cold 10 percent aqueous sodium hydroxide solution containing 2.294 grams (0.16 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 88 percent. The yield of the dye recrystallized from glacial acetic acid is 85 percent.

Example 9

This example performs diazotization of Broenner's acid. The general procedure explained above is used for this example.

A quantity of 3.593 grams (0.016 mol) of Broenner's acid is added to 20 milliliters of water containing 0.34 milliliter (0.053 mol) of nitric acid and 0.45 milliliter (0.016 mol) of sulfuric acid. Nitric oxide gas is allowed to flow into the closed air-filled reaction flask. Diazotization time is 22 minutes. Reverse addition to a cold 10 percent aqueous sodium hydroxide solution containing 2.376 grams (0.16 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 96 percent. The yield of the dye recrystallized from glacial acetic acid is 89 percent.

Example 10

This example performs diazotization of Para Base Sulfate. The general procedure explained above is used for this example.

A quantity of 4.52 grams (0.016 mol) of Para Base Sulfate is added to 20 milliliters of water containing 0.34 milliliter (0.053 mol) of nitric acid and 0.45 milliliter (0.016 mol) of sulfuric acid. Nitric oxide gas is allowed to flow into the air-filled reaction flask. Diazotization time is 15 minutes. Reverse addition to a cold 10 percent aqueous sodium hydroxide solution containing 2.417 grams (0.16 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 90 percent. The yield of the dye recrystallized from glacial acetic acid is 86 percent.

EXAMPLES 11 THROUGH 18

Diazotization with Nitric Oxide Gas and Air Flow (Reaction Scheme 2)

Example 11

This example produces 1-phenylazo-2-naphthol from aniline hydrochloride. The general procedure explained above is used for this example.

A quantity of 2.09 grams (0.016 mol) of aniline hydrochloride is added to 20 milliliters of water. Nitric oxide gas and air are allowed to flow into the reaction flask using two separate bubblers. Diazotization time is three minutes. Reverse addition to a cold 10 percent aqueous sodium hydroxide solution containing 2.395 grams (0.17 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 90 percent. The yield of the dye recrystallized from glacial acetic acid is 85 percent.

Example 12

This example produces 1-phenylazo-2-naphthol from aniline. The general procedure explained above is used for this example.

A quantity of 1.5 milliliters (0.016 mol) of aniline is added to 20 milliliters of water containing 0.45 milliliter (0.016 mol) of sulfuric acid. Nitric oxide gas and air are allowed to flow into the reaction flask through two separate bubblers. Diazotization time is three minutes. Reverse addition to a cold 10 percent aqueous sodium hydroxide solution containing 2.364 grams (0.16 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 94 percent. The yield of the dye recrystallized from glacial acetic acid is 86 percent.

Example 13

This example produces 4'-[2-hydroxy-naphthyl-1-azo]-azobenzol-sulfonic acid. The general procedure explained above is used for this example.

A quantity of 4.46 grams (0.016 mol) of 4-aminoazobenzene-4'-sulfonic acid is added to 20 milliliters of water containing 0.45 milliliter (0.016 mol) sulfuric acid. Nitric oxide gas and air are allowed to flow into the reaction flask through two separate bubblers. Diazotization time is five minutes. Reverse addition to a cold 10 percent aqueous sodium hydroxide solution containing 2.417 grams (0.17 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 90 percent. The yield of the dye recrystallized from glacial acetic acid is 85 percent.

Example 14

This example produces 1-o-tolylazo-2-naphthol. The general procedure explained above is used for this example.

A quantity of 1.75 milliliters (0.016 mol) of o-toluidine is added to 20 milliliters of water containing 0.45 milliliter (0.016 mol) of sulfuric acid. Nitric oxide gas and air are allowed to flow into the reaction flask through two separate bubblers. Diazotization time is five minutes. Reverse addition to a cold 10 percent aqueous sodium hydroxide solution containing 2.389 grams (0.17 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 81 percent. The yield of the dye recrystallized from glacial acetic acid is 86 percent.

Example 15

This example performs diazotization of para base sulfate. The general procedure explained above is used for this example.

A quantity of 4.522 grams (0.016 mol) of para base sulfate is added to 20 milliliters of water containing 0.45 milliliter (0.016 mol) of sulfuric acid. Nitric oxide gas and air are allowed to flow into the reaction flask through two separate bubblers. Diazotization time is five minutes. Reverse addition to a cold 10 percent aqueous sodium hydroxide solution containing 2.369 grams (0.16 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 91 percent. The yield of the dye recrystallized from glacial acetic acid is 85 percent and 83 percent at 60° C.

13

Example 16

This example performs diazotization of p-nitroaniline. The general procedure explained above is used for this example.

A quantity of 2.225 grams (0.016 mol) of p-nitroaniline is added to 20 milliliters of water containing 0.45 milliliter (0.016 mol) of sulfuric acid. Nitric oxide gas and air are allowed to flow into the reaction flask through two separate bubblers. Diazotization time is three minutes. Reverse addition to a cold 10 percent aqueous sodium hydroxide solution containing 2.404 grams (0.17 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 91 percent. The yield of the dye recrystallized from glacial acetic acid is 87 percent.

Example 17

This example performs diazotization of 4'-aminoacetophenone. The general procedure explained above is used for this example.

A quantity of 2.177 grams (0.016 mol) of 4'-aminoacetophenone is added to 20 milliliters of water containing 0.45 milliliter (0.016 mol) of sulfuric acid. Nitric oxide gas and air are allowed to flow into the reaction flask through separate bubblers. Diazotization time is four minutes. Reverse addition to a cold 10 percent aqueous sodium oxide solution containing 2.398 grams (0.17 mol) of 2-naphthol produces an instant red color. The solution is stirred for one hour and then allowed to crystallize for one hour in an ice bath. The resulting red crystals are vacuum filtered and dried overnight in a vacuum oven at 60° C. The crude yield of the dye is 91 percent. The yield of the dye recrystallized from glacial acetic acid is 85 percent.

Example 18

This example performs diazotization of Broenner's acid. The general procedure explained above is used for this example.

A quantity of 3.593 grams (0.016 mol) of Broenner's acid is added to 20 milliliters of water containing 0.45 milliliter (0.016 mol) of sulfuric acid. Nitric oxide gas and air are allowed to flow into the reaction flask through separate bubblers. Diazotization time is five minutes. Reverse addition to a cold 10 percent aqueous sodium hydroxide solution containing 2-naphthol produces an instant red color. The solution is stirred for one hour and then allowed to crystallize for one hour in an ice bath. The resulting red crystals are vacuum filtered and dried overnight in a vacuum oven at 60° C.

EXAMPLES 19 THROUGH 25

Diazotization with Other Oxidants

Examples 19 through 25 represent the invention. A diazotization procedure is performed in these examples with an oxidant other than air.

Example 19

This example produces 1-(4'-nitrobenzeneazo)-2-naphthol. The general procedure explained above is used for this example. This example uses sodium hypochlorite (NaOCl) as an oxidant.

14

A quantity of 3.51 grams (0.0254 mol) of 4-nitroaniline is added to 10 milliliters of warm water containing 1.4 milliliters (0.0256 mol) of concentrated sulfuric acid. This solution is stirred for 10 minutes until all of the amine dissolves. Then a quantity of 40 milliliters of distilled water is added, and the system is purged first with nitrogen and followed with nitric oxide. The flask is cooled in ice and stirred for 10 minutes before a quantity of 16.2 milliliters of a 5.25 percent sodium hypochlorite solution is added by a syringe. Nitric oxide gas is allowed to flow into the reaction flask which results in a 91.9 percent uptake of gas by the reaction. The reaction is stirred for 1.5 hours to ensure complete diazotization. Dropwise addition of 3.7 grams (0.0256 mol) of 2-naphthol and 20 milliliters of 10 percent sodium hydroxide solution to the diazotized product produces a bright red slurry. The mixture is warmed to room temperature and stirred overnight. After filtration, the product is recrystallized from a 4:1 ethanol to toluene mixture.

This example produces 6.9 grams of product compared to a theoretical yield of 7.5 grams. (% Yield=92%).

Example 20

This example produces 1-phenylazo-2-naphthol. The general procedure explained above is used for this example. This example uses hydrogen peroxide ($H_2O_2$) as an oxidant.

A solution of water and 1.5 milliliters (0.0275 mol) of concentrated sulfuric acid is stirred in a three-necked round bottom flask. The system is purged three times with nitrogen and then for one minute with nitric oxide. A quantity of 4.6 milliliters (0.054 mol) of aniline is added, and the mixture of 4.0 milliliters (0.0587 mol) of hydrogen peroxide is added by a syringe, and the mixture is stirred for five minutes. Nitric oxide gas is allowed to flow into the reaction flask. After complete nitric oxide uptake, the solution is stirred for 15 more minutes to ensure complete diazotization. A solution of 7.266 grams (0.0503 mol) of 2-naphthol in 25 milliliters of 10 percent sodium hydroxide is added dropwise with stirring. A bright red solution is produced. The solution is stirred overnight and filtered. The solid product is first recrystallized with glacial acetic acid and then with ethanol. Nitric oxide uptake is 166.9 percent in 13 hours.

This example produces 8.02 grams of product compared to a theoretical yield of 12.5 grams. (% Yield=64%)

Example 21

This example produces 1-phenylazo-2-naphthol. The general procedure explained above is used for this example. This example uses sodium iodate ($NaIO_3$) as an oxidant.

A three-necked round bottom flask containing a stirred 0.7 milliliter (0.012 mol) solution of aqueous sulfuric acid is purged with nitrogen for ten minutes. A quantity of 2.3 milliliters (0.025 mol) of aniline is added. This mixture is cooled in an ice bath and purged with nitric oxide for one minute. A quantity of 1.82 grams (0.009 mol) in 20 milliliters of water sodium iodate solution is added by a syringe and stirred for five minutes. Nitric oxide at one atmosphere of pressure is introduced into the reaction flask and the uptake is monitored volumetrically. After 10 hours, nitrogen is passed through the system. The reaction is passed through the system. The reaction mixture is stirred for 30 minutes to ensure complete diazotization. A quantity of 3.767 grams (0.026 mol) of 2-naphthol in 20 milliliters of a 10 percent sodium hydroxide solution is added and produces a pale orange slurry. The reaction mixture is warmed to room temperature and stirred overnight. The reaction product is filtered and recrystallized from ethanol. Nitric oxide uptake is 11 percent in 10 hours.

This example produces 0.528 gram of recrystallized product compared to a theoretical yield of 7.325 grams. (% Yield=7%)

Sodium iodate has a slightly favorable electrode potential for the oxidation of nitric oxide to nitrous acid. Diazotization proceeds very slowly and has a low nitric oxide uptake.

Example 22

This example produces 1-(4'-nitrobenzeneazo)-2-naphthol. The general procedure explained above is used for this example. This example uses sodium bromate ($NaBrO_3$) as an oxidant.

This example uses the same procedure as used in Example 21 except for the following variations. The reagents and their concentrations are:

p-nitroaniline is 4.25 g (0.030 mol);

Concentrated sulfuric acid is 2.5 ml (0.045 mol);

Sodium bromate is 1.66 g (0.011 mol) in 40 ml of water; and 2-naphthol is 4.202 g (0.028 mol) in 20 ml 10 percent NaOH solution.

The reaction is quenched after six hours and allowed to stir for 15 minutes to ensure complete diazotization.

Nitric oxide uptake in this example is 230 milliliters in six hours compared to a theoretical uptake of 672 milliliters. The example produces 1.720 grams of product.

Sodium bromate has a favorable electrode potential for the oxidation of nitric oxide to nitrous acid. When added to anilinium sulfate, the partial oxidation of aniline to aniline black results. This reaction is confirmed by TLC analysis.

Example 23

This example produces 1-phenylazo-2-naphthol. The general procedure explained above is used for this example. This example uses sodium sulfate ($Na_2SO_4$) as an oxidant.

This example uses the same procedure as used in Example 21 except for the following variations. The reagents and their concentrations are:

Aniline is 2.4 ml (0.026 mol);

Concentrated sulfuric acid is 0.8 ml (0.014 mol);

Sodium sulfate is 1.955 g (0.013 mol) in 209 ml water; and 2-naphthol is 3.730 g (0.025 mol) in 20 ml 10 percent NaOH solution.

The reaction is quenched after seven hours.

Nitric oxide uptake in this example is 100 milliliters in seven hours compared to a theoretical uptake of 560 milliliters. A very pale orange product is observed. Thin-layer chromatography analysis shows the presence of excess coupler (2-naphthol) and a very faint dye. Even upon recrystallization pure dye can not be obtained. The amount of product is negligible.

Sodium sulfate has an unfavorable electrode potential for the oxidation of nitric oxide to nitrous acid. A resulting low uptake or consumption of nitric oxide occurs.

Example 24

This example produces 1-phenylazo-2-naphthol. The general procedure explained above is used for this example. This example uses potassium chlorate ($KClO_3$) as an oxidant.

This example uses the same procedure as used in Example 21 except for the following variations. The reagents and their concentrations are:

Aniline is 2.3 ml (0.025 mol);

Concentrated sulfuric acid is 0.8 ml (0.014 mol);

Potassium chlorate is 1.034 g (0.0084 mol) in 20 ml water; and 2-naphthol is 3.635 g (0.025 mol) in 20 ml 10 percent NaOH solution.

The reaction is quenched after nine hours.

Nitric oxide uptake in this example is 570 milliliters in nine hours compared to a theoretical uptake of 560 milliliters. The example produces 2.716 grams of product with another 0.616 grams of product after recrystallization.

A pale orange product is observed. Thin-layer chromatography analysis shows the presence of coupler (2-naphthol) and the dye. Recrystallization is performed twice with an ethanol and water mixture to obtain the pure product.

Example 25

This example produces 1-phenylazo-2-naphthol. The general procedure explained above is used for this example. This example uses sodium perchlorate ($NaClO_4$) as an oxidant.

This example uses the same procedure as used in Example 21 except for the following variations. The reagents and their concentrations are:

Aniline is 2.8 ml (0.03 mol);

Concentrated sulfuric acid is 1.0 ml (0.018 mol);

Sodium perchlorate is 1.855 g (0.015 mol) in 10 ml water; and 2-naphthol is 4.301 g (0.03 mol) in 20 ml 10 percent NaOH solution.

The reaction is quenched after three hours and is stirred for 15 minutes to ensure complete diazotization.

Nitric oxide uptake in this example is 645 milliliters compared to a theoretical uptake of 672 milliliters. The example produces 4.80 grams of product compared to a theoretical yield of 8.79 grams. (% Yield=55%)

The yield of product in this example is low, but nitric oxide uptake with sodium perchlorate is comparatively faster than it is with most other oxidants. Thin-layer chromatography analysis of the bright orange product indicates a faint presence of 2-naphthol. Recrystallization with ethanol gives a pure product.

What is claimed is:

1. A process for diazotizing an amine comprising the steps of:

oxidizing nitric oxide in solution with an oxidizing agent having a half cell potential sufficient to generate a diazotizing agent from said solution to maintain an equilibrium concentration of a diazotizing agent; and reacting a primary aromatic amine in situ with said diazotizing agent in said solution; wherein the diazotization is performed according to the formula:

$$4HX + 4ArNH_2 + 4NO + O_2 \rightleftharpoons 4ArN_2^+X^- + 6H_2O$$

where $X^-$ represents the anion of any strong mineral acid and AR represents an aromatic group.

2. The process of claim 1, wherein said oxidizing agent is selected from the group consisting of oxygen, hydrogen peroxide, sodium hypochlorite, potassium chlorate, sodium perchlorate, sodium bromate, sodium iodate, and mixtures thereof.

3. A process for diazotizing an amine comprising the steps of:

passing nitric oxide through an aqueous mixture solution of a primary aromatic amine;

introducing into the oxide-containing aqueous solution a sufficient concentration of a selected oxidizing agent having a half cell potential sufficient to generate a diazotizing agent from said solution to maintain an equilibrium concentration of a diazotizing agent; and maintaining said equilibrium concentration of said diazotizing agent to diazotize said primary aromatic amine; wherein the diazotization is performed according to the formula:

$$4HX + 4ArNH_2 + 4NO + O_2 \rightleftharpoons 4ArN_2^+X^- + 6H_2O$$

where $X^-$ represents the anion of any strong mineral acid and Ar represents an aromatic group.

4. The process of claim 1, wherein said amine is of the formula:

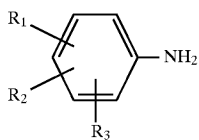

wherein $R_1$, $R_2$, and $R_3$ are independently selected from the group consisting of hydrogen, —$SO_3H$, —$CO_2H$, $C_1$–$C_6$ alkyl, $C_1$–$C_6$ alkoxy, halogen $C_2$–$C_6$ alkanoylamino, unsubstituted or substituted arylsulfonyl, sulfatoethyl sulfonyl, aryloxy, arylcarbonyl, phenylazo, naphthylazo, nitro radicals, and radicals of the formula

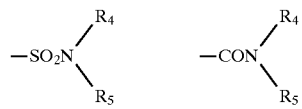

wherein $R_4$ and $R_5$ are $C_1$–$C_6$ alkyl or cycloalkyl or $R_4$ and $R_5$ constitute together a cyclic alkyl, cyclic alkyether, or cyclic alkylamine.

5. The process of claim 1, wherein said amine is of the formula:

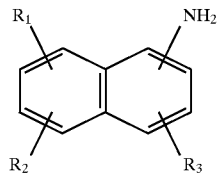

wherein $R_1$, $R_2$, and $R_3$ are independently selected from the group consisting of hydrogen, —$SO_3H$, —$CO_2H$, $C_1$–$C_6$ alkyl, $C_1$–$C_6$ alkoxy, halogen $C_2$–$C_6$ alkanoylamino, unsubstituted or substituted arylsulfonyl, sulfatoethyl sulfonyl, aryloxy, arylcarbonyl, phenylazo, naphthylazo, and nitro radicals.

6. The process of claim 1, wherein said amine is of the formula:

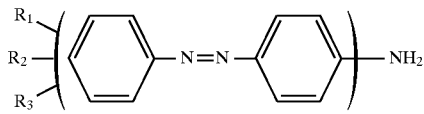

wherein $R_1$, $R_2$, and $R_3$ are independently selected from the group consisting of hydrogen, —$SO_3H$, —$CO_2H$, $C_1$–$C_6$ alkyl, $C_1$–$C_6$ alkoxy, halogen $C_2$–$C_6$ alkanoylamino, unsubstituted or substituted arylsulfonyl, sulfatoethyl sulfonyl, aryloxy, arylcarbonyl, phenylazo, naphthylazo, and nitro radicals.

7. The process of claim 4, wherein said oxidizing agent is selected from a group consisting of oxygen, hydrogen peroxide, sodium hypochlorite, potassium chlorate, sodium perchlorate, sodium bromate, sodium iodate and mixtures thereof.

8. The process of claim 5, wherein said oxidizing agent is selected from the group consisting of oxygen, hydrogen peroxide, sodium hypochlorite, potassium chlorate, sodium perchlorate, sodium bromate, sodium iodate and mixtures thereof.

9. The process of claim 6, wherein said oxidizing agent is selected from the group consisting of oxygen, hydrogen peroxide, sodium hypochlorite, potassium chlorate, sodium perchlorate, sodium bromate, sodium iodate and mixtures thereof.

10. A process for diazotizing an amine comprising the steps of:

feeding a primary aromatic amine into an aqueous solution;

passing nitric oxide through said aqueous solution of said primary aromatic amine at ambient temperature or lower;

introducing into said oxide-containing aqueous solution a sufficient concentration of an oxidizing agent of said nitric oxide to maintain an equilibrium concentration of a diazotizing agent, said oxidizing agent having a half cell potential sufficient to generate a diazotizing agent from said solution and being selected from the group consisting of nitric acid, oxygen, hydrogen peroxide, sodium hypochlorite, potassium chlorate, sodium perchlorate, sodium bromate, sodium iodate, and mixtures thereof; and maintaining said equilibrium concentration of said diazotizing agent to diazotize said primary aromatic amine; wherein the diazotization is performed according to the formula:

$$4HX + 4ArNH_2 + 4NO + O_2 \rightleftharpoons 4ArN_2^+X^- + 6H_2O$$

where $X^-$ represents the anion of any strong mineral acid and Ar represents an aromatic group.

* * * * *